United States Patent
Tanner et al.

[19]

[11] Patent Number: 5,972,175
[45] Date of Patent: Oct. 26, 1999

[54] CATALYTIC MICROWAVE CONVERSION OF GASEOUS HYDROCARBONS

[75] Inventors: Dennis D. Tanner; Qizhu Ding, both of Edmonton, Canada

[73] Assignee: Governors of the University of Alberta, Edmonton, Canada

[21] Appl. No.: 09/122,515

[22] Filed: Jul. 24, 1998

[51] Int. Cl.$^6$ .................................................. C01B 25/00
[52] U.S. Cl. .................................. 204/157.43; 204/157.15
[58] Field of Search ........................... 204/157.43, 157.3, 204/157.47, 157.52, 157.15, 157.6

[56] References Cited

U.S. PATENT DOCUMENTS

| | | | |
|---|---|---|---|
| 4,574,038 | 3/1986 | Wan | 204/162 |
| 4,729,891 | 3/1988 | Kulkarni | 423/650 |
| 4,975,164 | 12/1990 | Ravella et al. | 204/156 |
| 5,025,912 | 6/1991 | Murphy | 204/157.15 |
| 5,131,993 | 7/1992 | Suib et al. | 204/168 |
| 5,181,998 | 1/1993 | Murphy et al. | 204/157.15 |
| 5,277,773 | 1/1994 | Murphy | 204/168 |
| 5,328,577 | 7/1994 | Murphy | 204/168 |
| 5,472,581 | 12/1995 | Wan | 204/157.6 |

FOREIGN PATENT DOCUMENTS

| | | |
|---|---|---|
| 0433591A2 | 7/1991 | European Pat. Off. . |
| PCT/US91/04622 | 6/1991 | WIPO . |

OTHER PUBLICATIONS

Dimerization of Methane Through Microwave Plasmas, J. Huang, SL Suib, American Chemical Society, 1993. No Month.

A Direct, Continous, Low–Power Catalytic Conversion of Methane to Higher Hydrocarbons Via Microwave Plasmas, SL Suib, RP Zerger, Journal of Catalysis 139, 383–381, 1993. No Month.

*Primary Examiner*—Kathryn Gorgos
*Assistant Examiner*—Jonathan Brown
*Attorney, Agent, or Firm*—Paul W. Zimmerman

[57] ABSTRACT

The method of the present invention is for producing at least hydrogen from a gaseous hydrocarbon. The gaseous hydrocarbon is selected from the group consisting of methane, ethane, butane, propane and combinations thereof. The method proceeds by exposing the gaseous hydrocarbon with the supported catalyst to microwave radiation. The supported catalyst has a support of a lattice of a non-metallic amorphous solid and at least one catalytic metal having atoms interspersed throughout the lattice of the support. A preferred embodiment is a lattice of carbon with at least one catalytic metal interspersed throughout the lattice. Examples include char.

20 Claims, 1 Drawing Sheet

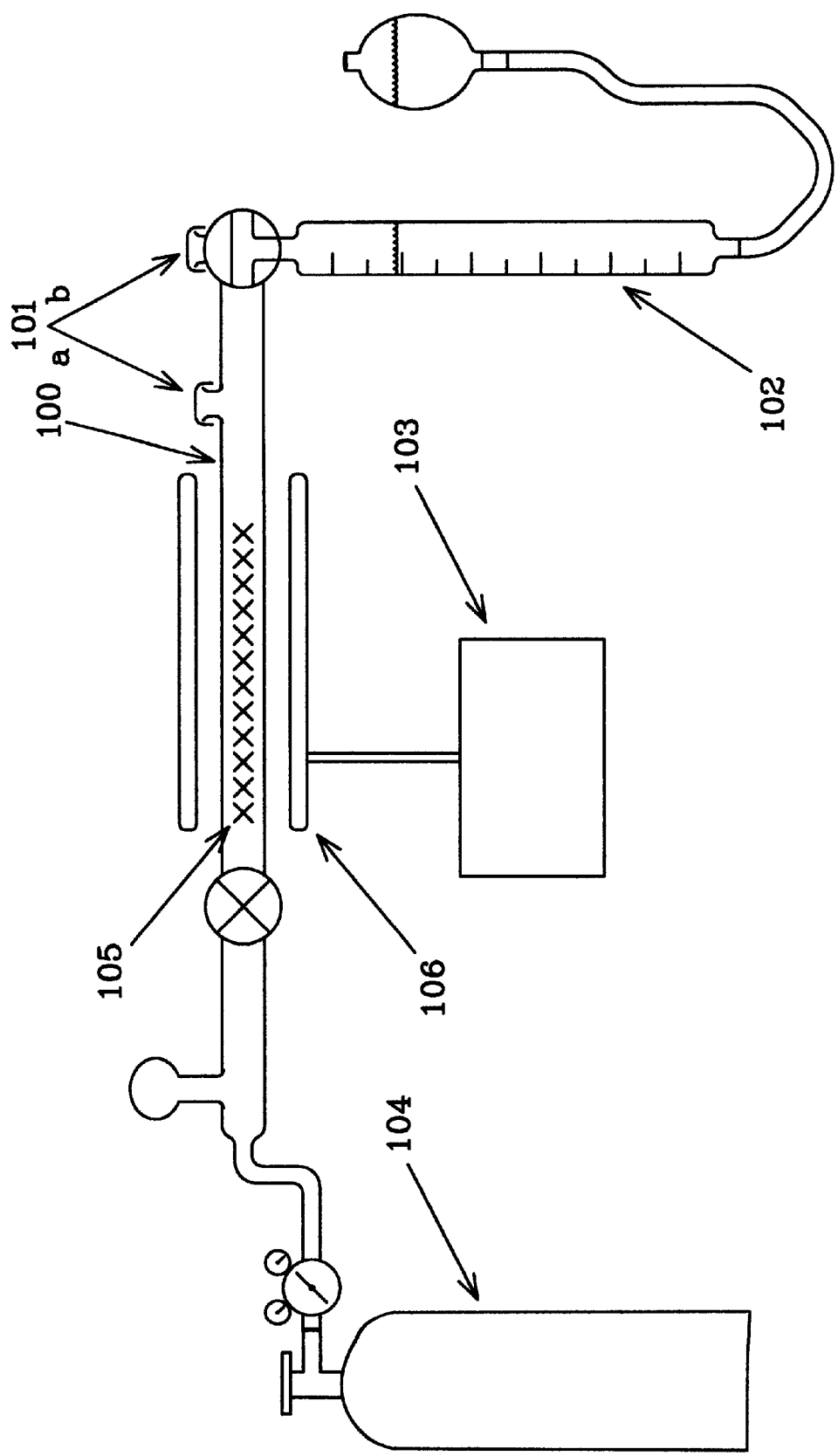

CATALYTIC MICROWAVE CONVERSION OF GASEOUS HYDROCARBONS

FIELD OF THE INVENTION

The present invention is a method of using a supported catalyst for catalytic microwave conversion of gaseous hydrocarbons. More specifically, the method is selective toward hydrogen and ethylene.

BACKGROUND OF THE INVENTION

Conversion of natural gas or gaseous hydrocarbons of methane, ethane, butane, propane and combinations thereof is useful in the commodity chemical industry. Such conversion utilizing microwave energy has been described in U.S. Pat. No. 3,663,394 and in U.S. Pat. No. 4,574,038.

More recently, U.S. Pat. No. 4,975,164 to Ravella et al. mentions microwave conversion of gaseous hydrocarbon (butane) by using "plasma initiators" that are metal (e.g. tungsten, iron, nickel, copper, etc.) with tungsten preferred or non-metal (e.g. carbon, alumina, metal oxides, metal nitrides, metal sulfides, etc.) with carbon preferred. The plasma initiator is used singly or as a spaced plurality with at least 0.25 cm spacing between plasma initiators. Ravella et al. require the presence of hydrogen to maintain activity of the plasma initiator. The mole ratio of plasma initiator (tungsten) to gaseous hydrocarbon (butane) used by Ravella et al. was from 0.0032 to 0.0048 depending upon the reaction time.

U.S. Pat. No. 4,574,038 to Wan discusses microwave conversion of a gaseous hydrocarbon (methane) by using a metal powder catalyst. Wan requires a mole ratio of metal powder catalyst to gaseous hydrocarbon (methane) of about 0.4. Wan pre-treats the metal powder with hydrogen prior to performing conversion.

U.S. Pat. No. 5,472,581 to Wan discusses microwave conversion of a gaseous hydrocarbon (methane) to a product that is primarily acetylene by using pulsed microwave energy of at least 1.5 kW (1500 W).

It is a long felt need in the art of microwave conversion of gaseous hydrocarbons to perform the conversion without hydrogen either added to the gaseous hydrocarbon or used to pre-treat the catalyst. It is a further long felt need to reduce the quantity of catalyst material necessary for the conversion.

SUMMARY OF THE INVENTION

The present invention is a method for microwave conversion of a gaseous hydrocarbon for producing at least hydrogen. The gaseous hydrocarbon is selected from the group consisting of methane, ethane, butane, propane and combinations thereof. The method proceeds by exposing the gaseous hydrocarbon in the presence of a supported catalyst to microwave radiation. The improvement is two-fold wherein (1) a ratio of the catalyst metal to the gaseous hydrocarbon is less than 0.003 mole catalyst metal per mole of gaseous hydrocarbon, and the gaseous hydrocarbon has either no hydrogen gas or an amount of hydrogen gas that is ineffective to the producing, and (2) the microwave energy is sufficiently low to be selective for hydrogen and ethylene over acetylene.

Advantages of the catalyst and method of the present invention include (1) natural sources of char are easily and inexpensively obtained (2) no addition of catalytic metal is needed, (3) the amount of catalytic metal is less than presently used for microwave conversion, (4) spent supported catalyst material is environmentally friendly (ie is not defined as a hazardous waste), and (5) no addition or use of separate hydrogen gas is needed either for activation or production.

Accordingly, it is an object of the present invention to provide a method of microwave conversion of a gaseous hydrocarbon using an amount of catalytic metal in a ratio less than 0.003 mole catalytic metal to mole of gaseous hydrocarbon.

It is another object of the present invention to provide a method of microwave conversion of a gaseous hydrocarbon that does not require added hydrogen gas.

It is a further object of the present invention to provide a method of microwave conversion of a gaseous hydrocarbon that is selective toward hydrogen and ethylene over acetylene.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 1 is a schematic of a laboratory apparatus for demonstrating the present invention.

DESCRIPTION OF THE PREFERRED EMBODIMENT(S)

The supported catalyst used in the present invention is for microwave conversion of a gaseous hydrocarbon has
 (a) a support of a lattice of a non-metallic amorphous solid; and
 (b) at least one catalytic metal having atoms interspersed throughout the lattice of the support.

Non-metallic amorphous solids include but are not limited to carbon, alumina, manganese dioxide, magnetite, nickel oxide, iron oxide, calcium aluminize, cobalt oxide, chromium nitride, iron sulfide, copper sulfide and combinations thereof.

Catalytic metal includes but is not limited to chromium (Kr), copper (Cu), iron (Fe), nickel (Ni), lead (Pb), zinc (Zn), boron (B), barium (Ba), magnesium (Mg), strontium (Sr), titanium (Ti), vanadium (V), phosphorus (P), manganese (Mn), molybdenum (Mo), silicon (Si), silver (Ag), aluminum (Al), cadmium (Cd), cobalt (Co) and combinations thereof. Unreactive elements are calcium (Ca), potassium (K), sodium (Na) and combinations thereof. The presence of unreactive elements is not harmful to the conversion of the gaseous hydrocarbon.

In a preferred embodiment, a ratio of at least one catalytic metal to the support plus at least one catalytic metal is less than 0.01 mg/10 mg support, preferably less than 0.002 mg/10 mg support. In a most preferred embodiment, the support and catalytic metal occur together wherein the non-metallic amorphous solid is carbon, for example a char. The char may be wood char, charcoal, and combinations thereof. Wood char may be produced by exposing wood in a non-oxidative atmosphere to an elevated temperature. For example, slivers of white pine placed in a nitrogen atmosphere and heated to 800° C. produce an acceptable supported catalyst. Charcoal may be obtained from any source, but is most commonly obtained from charcoal, petroleum charcoal and combinations thereof. Table 1 shows an analysis of non-carbon elements present in the three chars.

TABLE 1

Analysis of Chars in Mass of Element per Mass of Char (mg/10 mg Char)[a]

| Element | White Pine Char | Wood Charcoal | Petroleum Charcoal |
|---------|-----------------|---------------|--------------------|
| Al | NA | 0.00775 | 0.0078 |
| Cd | NA | 0 | 0 |
| Co | NA | 0.0003 | 0.0001 |
| Cr | 0.00035 | 0.00195 | 0 |
| Cu | 0.00115 | 0.00145 | 0.001 |
| Fe | 0.00155 | 0.00035 | 0.00505 |
| Ni | 0.00585 | 0.0059 | 0.00015 |
| Pb | 0.00035 | 0 | 0 |
| Zn | 0.001 | 0.0061 | 0.0267 |
| B | 0.0016 | 0 | 0 |
| Ba | 0.00095 | 0.0264 | 0.00025 |
| Ca | 0.0464 | 26.9135 | 0.3823 |
| K | 0.4628 | 0.53715 | 0.08175 |
| Mg | 0.02145 | 0.0836 | 0.0345 |
| Sr | 0.00095 | 0.0934 | 0.00105 |
| Ti | 0 | 0 | 0 |
| V | 0.00005 | 0.00055 | 0.0001 |
| Na | 0.04765 | 0.0151 | 0.4673 |
| P | 0.0559 | 0.1431 | 0 |
| Mn | 0.0004 | 0.13575 | 0.0002 |
| Mo | 0.00075 | 0.0002 | 0.0002 |
| Si | 0 | 0 | 0 |
| Ag | 0.0007 | 0.00085 | 0 |

[a]10 mg of char was digested in 30 mL of Concentrated $HNO_3$. The $HNO_3$ Solution was evaporated to white powder. The white powder was dissolved in 50 mL water for ICP (Ion-Coupled Plasma) analysis. Results are cited in units of mg element/10 mg char.

The method of producing at least hydrogen from a gaseous hydrocarbon selected from the group consisting of methane, ethane, butane, propane and combinations thereof is practiced by placing the gaseous hydrocarbon with a catalyst and exposing them to microwave radiation. The invention is an improvement wherein the catalyst is the supported catalyst described above having a carrier with an amount of a catalyst metal that in a ratio of the catalyst metal to the gaseous hydrocarbon is less than 0.003 mole catalyst metal per mole of gaseous hydrocarbon, and substantially no hydrogen gas is provided, with microwave energy sufficiently low, e.g. less than 1000 W, and preferably less than about 50 W, favoring production of hydrogen and ethylene compared to acetylene. No hydrogen gas is needed for refreshing or activating the catalyst. Accordingly, "substantially no hydrogen gas" is either no hydrogen gas or an amount of hydrogen gas that is ineffective for the producing. Ineffective includes both not beneficial or not harmful.

Conditions for the method are atmospheric pressure, ambient temperature, and microwave energy at about 2,450 MHz. It is preferred that the amount of water in the feedstock be less than a saturation quantity of water, more preferably a relative humidity less than about 20%. In some cases it is desirable to provide a heat exchanger to remove thermal energy from microwave energy conversion. It is further observed that excessive microwave energy can produce excessive heat thereby degrading the desired reaction product(s).

A laboratory apparatus is shown in FIG. 1. The supported catalyst 105 is placed within a reaction vessel 100. Feedstock gaseous hydrocarbon is supplied from a feedstock supply vessel 104. A microwave antenna 106 is energized from a microwave generator 103. Collection plates 101a, 101b and burette 102 may be used for analysis.

EXAMPLE 1

An experiment was conducted to demonstrate the method of the present invention using char as the supported catalyst for converting ethane to ethylene. Conditions were atmospheric pressure, ambient temperature and a microwave generator at 2,450 MHz. Several runs wherein the feed of ethane was saturated with water resulted in much less conversion. Runs with water saturated ethane were done with fresh char. Results are shown in Table E1-1.

Tests with Petroleum based char produced similar results as in Table E1-1.

TABLE E1-1

Conversion of Ethane (5 mL/min) Using White Pine Charcoal (0.3 g)

The products of the microwave assisted reactions of ethane with a carbon catalyst.[a]

| Reaction | Ethane passed (mL) | ΔV (mL)[b] | Products (mol × 10$^4$) | | | | | | |
|----------|--------|--------|------|------|--------|----------|--------|----------|----------|
| | | | $H_2$ | CO | $CH_4$ | $C_2H_4$ | $CO_2$ | $C_2H_6$ | $C_2H_2$ |
| 1 | 8.0 | 13.0 | 1.71 | 0.47 | 0.16 | 0.41 | 0.57 | 1.82 | 0.03 |
| 2 | 14.5 | 15.5 | 3.22 | 0.62 | 0.12 | 0.43 | 0.56 | 1.05 | 0.19 |
| 3 | 19.5 | 19.0 | 4.25 | 0.76 | 0.15 | 0.30 | 0.38 | 1.59 | 0.15 |
| 4 | 24.5 | 24.0 | 4.12 | 0.86 | 0.33 | 0.86 | 0.38 | 2.68 | 0.38 |
| 5 | 30.0 | 30.0 | 6.72 | — | 2.52 | 0.24 | 0.24 | 2.16 | 0.12 |

[a]Char (White Pine) sticks 0.1 cm–0.7 cm in length; Ethane flow rate 5 mL/min.
[b]The change in volume in the gas burette after the microwave reaction.

| Reaction | Ethane conversion (%) | $H_2$/ (Ethane) reacted[a] | $C_2H_4$/ (Ethane) reacted | Total product/ (Ethane) reacted[a] |
|----------|-----------------------|---------------------------|-----------------------------|-------------------------------------|
| 1 | 43.1 | 92.7 | 29.7 | 171.7 |
| 2 | 81.9 | 55.3 | 9.10 | 85.4 |

TABLE E1-1-continued

Conversion of Ethane (5 mL/min) Using White Pine Charcoal (0.3 g)

| | | | | |
|---|---|---|---|---|
| 3 | 79.6 | 60.5 | 4.83 | 80.5 |
| 4 | 72.6 | 50.9 | 12.1 | 83.4 |
| 5 | 82.0 | 63.2 | 2.43 | 92.6 |

[a] The yields of hydrogen, carbon dioxide and carbon monoxide were corrected for the control reaction where no ethane was passed.

EXAMPLE 2

An experiment was conducted to demonstrate conversion of methane using the char and conditions set forth in Example 1. Results for seven (7) reactions are shown in Table E2-1. Hydrogen, ethylene and unconverted methane were produced. Accordingly, a larger amount of catalyst bed would increase overall conversion, as would a methane recycle loop.

The seven reactions were carried out separately but sequentially on the same sample of catalyst.

In reaction 1, 10 ml of methane was passed with microwave irradiation over 2 minutes. The gases were collected in the burette and the change in volume ($\Delta V$) was measured. The gases were then allowed to mix throughout the reactor with the microwave power off, and mole fractions of the components determined by gc analysis. The moles of gases in the mixture were calculated by assuming ideal gas behavior at 740 mm pressure and 23 degrees C. temperature. Then, for reaction 2, all the gases were evacuated, the system was flushed with nitrogen and then 20 mL of methane was passed with microwave irradiation, and the analysis repeated. This was repeated through seven reactions with successively increasing amounts of methane.

The moles of products produced were derived from the stated volume of methane. For example, in experiment 7, 70 ml of methane were used to give the moles of products shown.

TABLE E2-1

Methane (5 mL/min) Conversion with Pine Char

The products of the microwave assisted reactions of methane with a carbon catalyst.[a]

| Reaction | Methane passed (mL) | $\Delta V$ (mL)[b] | Products (mol × $10^4$) | | | | | | |
|---|---|---|---|---|---|---|---|---|---|
| | | | $H_2$ | CO | $CH_4$ | $C_2H_4$ | $CO_2$ | $C_2H_6$ | $C_2H_2$ |
| 1 | 10 | 13.5 | 2.11 | 0.70 | 0.11 | 1.13 | 1.35 | — | — |
| 2 | 20 | 16.0 | 2.83 | 1.21 | 0.55 | 1.10 | 0.78 | — | tr. |
| 3 | 30 | 19.0 | 4.9 | 0.76 | 0.30 | 0.76 | 0.83 | — | tr. |
| 4 | 40 | 28.0 | 6.6 | — | 0.28 | 1.20 | 0.33 | — | 0.03 |
| 5 | 50 | 39.0 | 9.4 | — | 3.50 | 0.80 | 0.16 | — | 0.16 |
| 6 | 60 | 44.0 | 8.7 | — | 7.83 | 0.89 | 0.18 | — | 0.18 |
| 7 | 70 | 53.0 | 8.1 | — | 12.1 | 0.42 | 0.02 | 0.06 | 0.64 |

[a] Char (White Pine) sticks 0.1 cm–0.7 cm in length; Methane flow rate 5 mL/min.
[b] The change in volume in the gas burette after the microwave reaction.

| Reaction | $CH_4$ conversion (%) | $H_2$/ ($CH_4$) reacted[a] | $2C_2H_4$/ ($CH_4$) reacted | Total product/ ($CH_4$) reacted[a,b] |
|---|---|---|---|---|
| 1 | 97.0 | 54.0 | 58.0 | 140.4 |
| 2 | 94.7 | 30.5 | 28.5 | 95.8 |
| 3 | 94.4 | 45.3 | 15.6 | 63.1 |
| 4 | 81.3 | 38.1 | 15.0 | 65.1 |
| 5 | 80.5 | 55.2 | 9.94 | 11.9 |
| 6 | 67.9 | 50.9 | 11.0 | 13.3 |
| 7 | 56.7 | 47.8 | 2.60 | 13.9 |

[a] The yields of hydrogen, carbon dioxide and carbon monoxide were corrected for the control reaction where no methane was passed.
[b] Total product = $CO + CO_2 + 2C_2H_4 + 2C_2H_6 + 2C_2H_2$ Results show a surprising order-of-magnitude increase of hydrogen and ethylene production with about 3% or less conversion to acetylene compared to Wan U.S. Pat. No. 5,472,581.

EXAMPLE 3

A third example of conversion of methane to ethylene and hydrogen is illustrated in Table E3-1. A sample of 0.3 g g catalyst produced from White Pine char which had been treated with a saturated solution of $NiCO_3$, before charring was exposed to a 5 mL/min stream of methane with microwave irradiation. The White Pine char (doped with $NiCO_3$) converted methane (80.2–99.4%) to hydrogen (70.4–133.8%) and ethylene (1.26–9.70%) with no acetylene.

TABLE E3-1

Conversion of methane by Ni doped catalyst

The products of the microwave assisted reactions of methane with a carbon catalyst[a]

| Reaction | Methane[b] passed (mL) | ΔV (mL)[c] | Products (mol × 10$^4$) | | | | | | |
|---|---|---|---|---|---|---|---|---|---|
| | | | $H_2$ | CO | $CH_4$ | $C_2H_4$ | $CO_2$ | $C_2H_6$ | $C_2H_2$ |
| 1 | 8.5  | 13.5 | 3.29 | 1.24 | 0.05 | 0.16 | 0.59 | — | — |
| 2 | 12.0 | 16.5 | 3.95 | 2.24 | 0.03 | 0.03 | 0.33 | — | — |
| 3 | 14.0 | 22.0 | 6.59 | 1.32 | 0.09 | —    | 0.70 | — | — |
| 4 | 23.5 | 36.0 | 11.2 | 2.16 | 0.86 | —    | tr.  | — | — |
| 5 | 27.5 | 42.0 | 12.4 | 2.01 | 2.18 | —    | —    | — | — |

[a]-The Pine wood sticks were soaked in a saturated solution of NiCO3 for 24 hours before charring. 0.3 g of char was used with a methane flow of 5 mL/min.
[b]-The measured volume of methane in a control experiment without microwave irradiation.
[c]-The increase of volume in the gas burette after the microwave reaction.

| Reaction | $CH_4$ conversion (%) | $H_2$/ $(CH_4)$ reacted[a] | $2C_2H_4$/ $(CH_4)$ reacted | Total product/ $(CH_4)$ reacted[a,b] |
|---|---|---|---|---|
| 1 | 98.5 | 86.7  | 9.70 | 48.7 |
| 2 | 99.4 | 70.4  | 1.26 | 45.2 |
| 3 | 98.4 | 110.7 | —    | 28.7 |
| 4 | 90.8 | 125.4 | —    | 22.0 |
| 5 | 80.2 | 133.8 | —    | 22.8 |

[a]-The yields of hydrogen, carbon dioxide and carbon monoxide were corrected for the control reaction where no methane was passed.
[b]-Total product = $CO + CO_2 + 2C_2H_4$

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of producing a product gas from a gaseous hydrocarbon selected from the group consisting of methane, ethane, butane, propane and combinations thereof, by placing the gaseous hydrocarbon with a catalyst and exposing them to microwave radiation, wherein the improvement comprises:
    providing an amount of a catalyst metal in a support that in a ratio of the catalyst metal to the gaseous hydrocarbon is less than 0.003 mole catalyst metal;
    said microwave radiation in an amount less than 1000 W; and
    providing either no hydrogen gas or an amount of hydrogen gas that is ineffective to the producing; wherein said product gas has less than 3 percent acetylene of the gaseous hydrocarbon.

2. The method as recited in claim 1, wherein said product gas includes ethylene.

3. The method as recited in claim 2, wherein after extended microwave exposure, only hydrogen is produced.

4. The method as recited in claim 1, wherein said microwave radiation is less than or equal to 50 W.

5. The method as recited in claim 1, wherein said supported catalyst comprises:
    (a) a support of a lattice of a non-metallic amorphous solid; and
    (b) at least one catalytic metal having atoms interspersed throughout the lattice of the support.

6. The method as recited in claim 5, wherein a ratio of said at least one catalytic metal to said support including the at least one catalytic metal is less than 0.01 mg/mg support.

7. The method as recited in claim 5, wherein said non-metallic amorphous solid is carbon.

8. The method as recited in claim 5, wherein said non-metallic amorphous solid is a char.

9. The method as recited in claim 8, wherein said char is selected from the group consisting of wood char, charcoal, and combinations thereof.

10. The method as recited in claim 9, wherein said charcoal is selected from the group consisting of wood charcoal, petroleum charcoal and combinations thereof.

11. A method of producing a product gas from a gaseous hydrocarbon selected from the group consisting of methane, ethane, butane, propane and combinations thereof, by placing the gaseous hydrocarbon with a catalyst and exposing them to microwave radiation, wherein the improvement comprises:
    said catalyst is a supported catalyst having (a) a support of a lattice of a non-metallic amorphous solid; and (b) at least one catalytic metal having atoms interspersed throughout the lattice of the support;
    said microwave radiation in an amount less than 1000 W; and
    providing either no hydrogen gas or an amount of hydrogen gas that is ineffective to the producing; wherein said product gas has less than 3 percent acetylene of the gaseous hydrocarbon.

12. The method as recited in claim 11, wherein said product gas includes ethylene.

13. The method as recited in claim 12, wherein after extended microwave exposure, only hydrogen is produced.

14. The method as recited in claim 11, wherein said microwave radiation is less than or equal to 50 W.

15. The method as recited in claim 11, wherein said at least one catalytic metal is present in an amount in a ratio of the at least one catalytic metal to the gaseous hydrocarbon is less than 0.003 mole catalytic metal.

16. The method as recited in claim 15, wherein a ratio of said at least one catalytic metal to said support including the at least one catalytic metal is less than 0.01 mg/mg support.

17. The method as recited in claim 15, wherein said non-metallic amorphous solid is carbon.

18. The method as recited in claim 15, wherein said non-metallic amorphous solid is a char.

19. The method as recited in claim 18, wherein said char is selected from the group consisting of wood char, charcoal, and combinations thereof.

20. The method as recited in claim 19, wherein said charcoal is selected from the group consisting of wood charcoal, petroleum charcoal and combinations thereof.

* * * * *

UNITED STATES PATENT AND TRADEMARK OFFICE
CERTIFICATE OF CORRECTION

PATENT NO. : 5,972,175
DATED : October 26, 1999
INVENTOR(S) : Tanner et al.

Page 1 of 1

It is certified that error appears in the above-identified patent and that said Letters Patent is hereby corrected as shown below:

<u>Column 2,</u>
Line 38, please remove the word "is".

Signed and Sealed this

Seventh Day of May, 2002

Attest:

Attesting Officer

JAMES E. ROGAN
*Director of the United States Patent and Trademark Office*